(12) United States Patent
McGuckin, Jr.

(10) Patent No.: US 10,548,756 B2
(45) Date of Patent: *Feb. 4, 2020

(54) TRANSFORMABLE ORTHOPEDIC BRACE FOR INJURY PREVENTION

(71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

(*) Notice: Subject to any disclaimer, the term of this patent is extended or adjusted under 35 U.S.C. 154(b) by 204 days.

This patent is subject to a terminal disclaimer.

(21) Appl. No.: 15/875,962

(22) Filed: Jan. 19, 2018

(65) Prior Publication Data

US 2018/0140449 A1 May 24, 2018

Related U.S. Application Data

(63) Continuation of application No. 14/578,370, filed on Dec. 20, 2014, now Pat. No. 9,889,033.

(60) Provisional application No. 61/940,406, filed on Feb. 15, 2014.

(51) Int. Cl.
*A61F 5/01* (2006.01)

(52) U.S. Cl.
CPC ...... *A61F 5/0104* (2013.01); *A61F 2210/008* (2013.01); *A61F 2210/0061* (2013.01); *A61F 2210/0085* (2013.01)

(58) Field of Classification Search
CPC .... A61F 5/0104; A61F 5/0106; A61F 5/0111; A61F 2210/008; A61F 2210/0085
See application file for complete search history.

(56) References Cited

U.S. PATENT DOCUMENTS

| 4,964,402 | A | 10/1990 | Grim |
| 6,066,017 | A | 5/2000 | Max |
| 6,289,889 | B1 | 9/2001 | Bell |
| 9,889,033 | B2* | 2/2018 | McGuckin, Jr. ...... A61F 5/0104 |
| 2009/0024065 | A1 | 1/2009 | Einarsson |
| 2011/0155141 | A1 | 6/2011 | Sawyer |
| 2013/0019374 | A1 | 1/2013 | Schwartz |
| 2014/0015176 | A1 | 1/2014 | Wetzel |

FOREIGN PATENT DOCUMENTS

| JP | 2007/260189 | 10/2007 |
| JP | 2013/202278 | 10/2013 |
| WO | WO 89/11259 | 11/1989 |
| WO | WO-2011/008934 A2 | 1/2011 |

OTHER PUBLICATIONS

EP 15 15 3885 European Search Report (dated Jun. 24, 2015).

* cited by examiner

*Primary Examiner* — Kristen Matter
(74) *Attorney, Agent, or Firm* — Neil D. Gershon

(57) ABSTRACT

An orthopedic brace for preventing injury to a wearer including a body having a series of liquid filled regions, the body having a first more flexible state wherein the liquid filled regions contain a liquid material and a second more rigid state wherein the liquid within the regions is hardened to a second harder state, the body transformable from the first state to the second state upon receiving a force which exceeds a predetermined value. A chemical reaction or an isothermal process can cause the phase change.

18 Claims, 10 Drawing Sheets

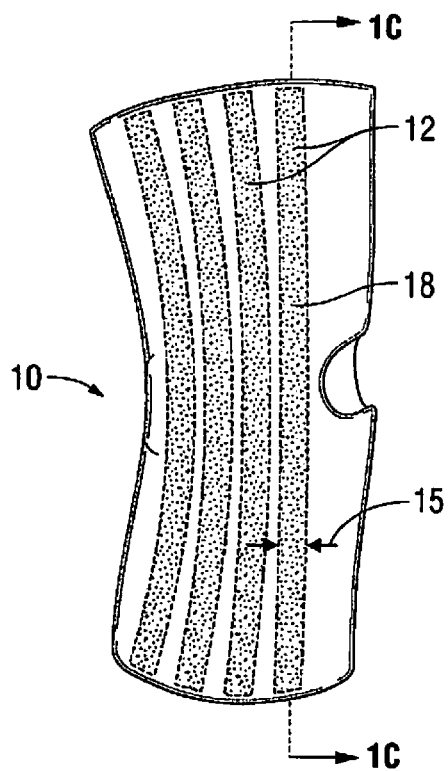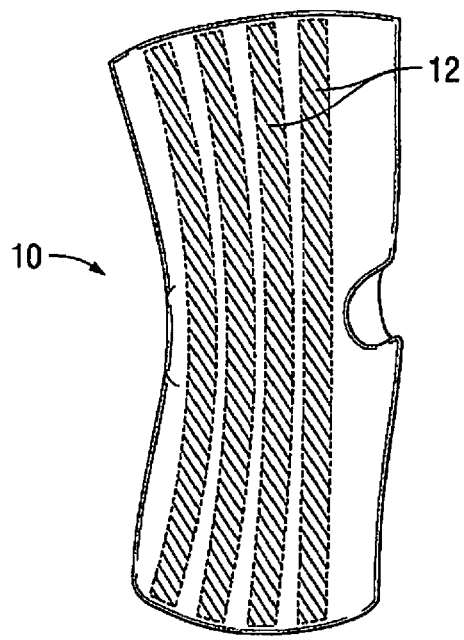
FIG. 1A  FIG. 1B
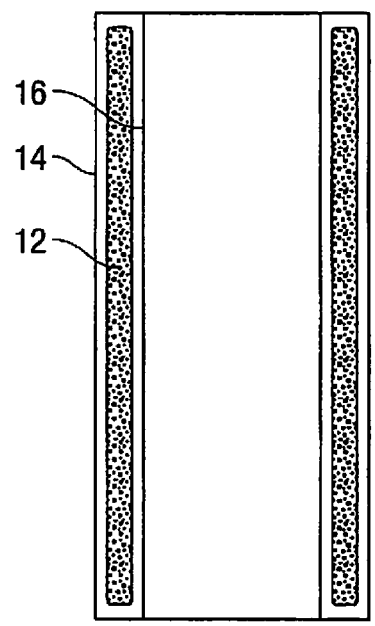
FIG. 1C

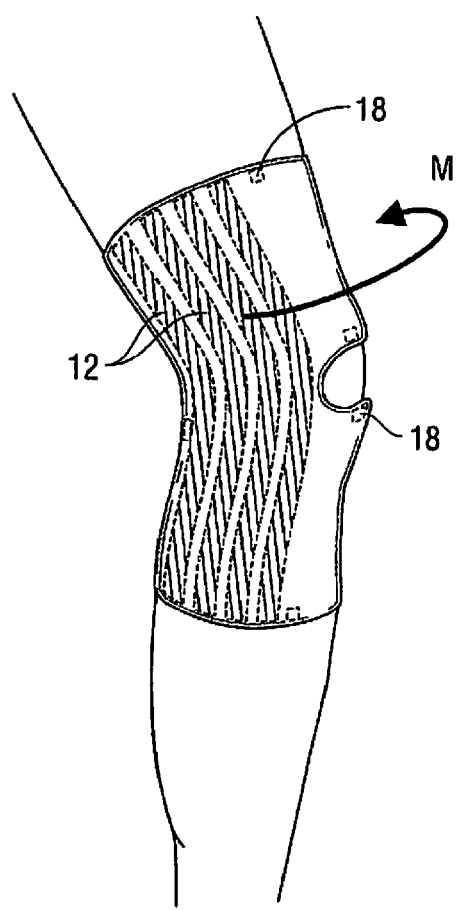 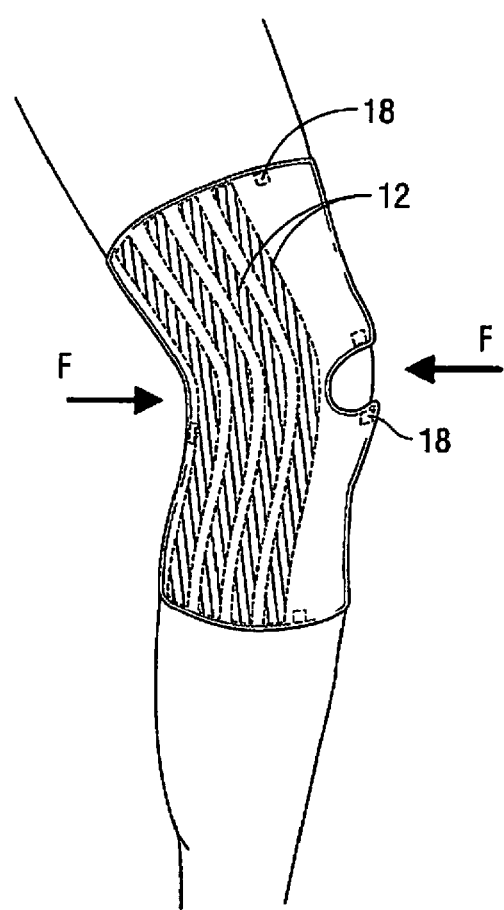
FIG. 5A  FIG. 5B

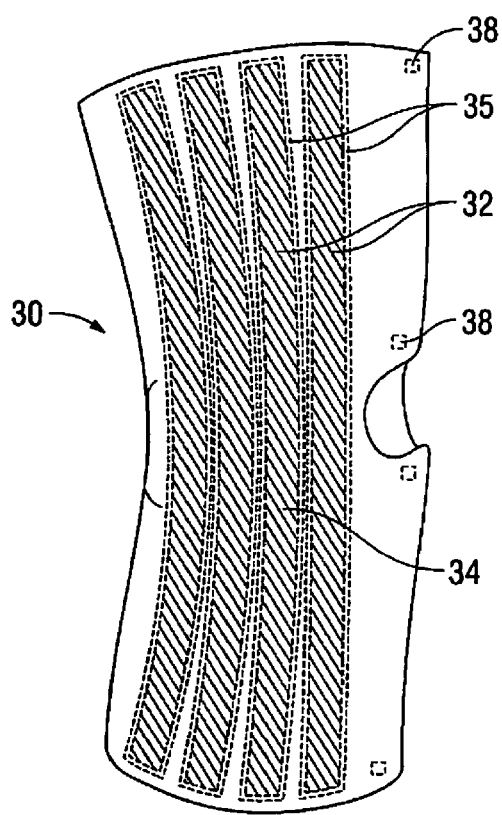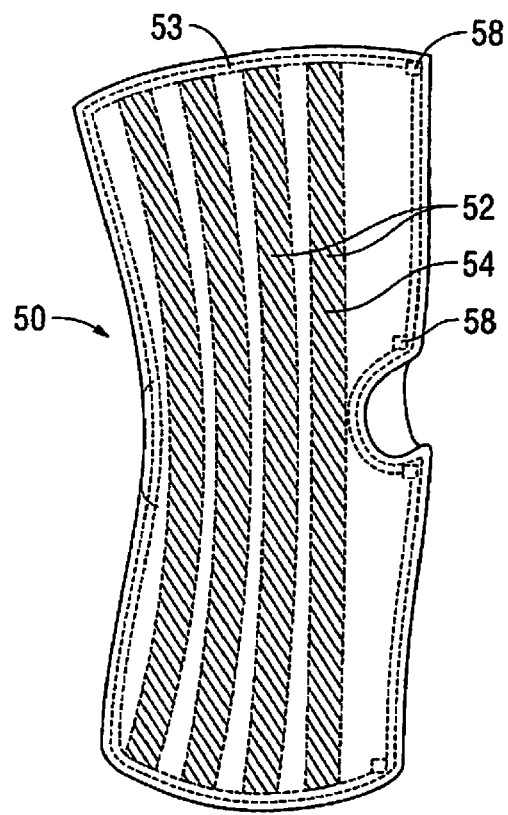
FIG. 6  FIG. 7

TRANSFORMABLE ORTHOPEDIC BRACE FOR INJURY PREVENTION

This application is a continuation of application Ser. No. 14/578,370, filed Dec. 29, 2017, which claims priority from provisional application Ser. No. 61/940,406, filed Feb. 15, 2014. The entire contents of each of these applications are incorporated herein by reference.

BACKGROUND

Technical Field

This application relates to an orthopedic brace for injury prevention and more particularly to an orthopedic brace that can be transformed from a softer to harder state to prevent injury.

Background of Related Art

Braces for use to protect the knee, ankle or other parts of the body are known. These braces are typically composed of a rigid material designed to prevent injury to the knee or ankle upon impact by an external force. The braces are also designed to prevent injury caused by an internal force such as severe or sudden knee or ankle rotation. That is, since external or internal forces cause abnormal stress or strain on ligaments and/or joints, and can lead to tissue tear or rupture, or other damage, these prior braces are designed to provide a rigid support to limit such damage.

Although known rigid braces can protect the knee or ankle, they severely inhibit motion. They are also stiff and heavy and therefore uncomfortable to wear. Consequently, people oftentimes will not wear such uncomfortable mobile affecting braces, and accept the risk of injury. Additionally, oftentimes it is only necessary to have such support if the knee or ankle is subject to excessive stress, but not required during normal activity. However since the user does not know when such stress might occur, the user is forced to wear the cumbersome brace at all times in anticipation of such excessive force and thus unnecessarily has his or her mobility reduced. Alternatively, due to the reduced mobility and discomfort, the user might decide not to wear the brace, taking the risk of severe injury if the knee or ankle is impacted without the support of the brace.

For athletes the choice is even more difficult as they need to choose between a) not wearing a brace and subjecting themselves to risk of injury, and potentially career ending injury, or b) wearing a motion restricting brace which adversely affects their athletic performance. In some instances, because of the rigid brace, the athlete may not even be able to participate in the athletic activity.

Therefore, it would be advantageous to provide a brace that is sufficiently lightweight and flexible so as to be comfortable to the user and not adversely affect motion and mobility, while still providing maximum protection to the knee or ankle to prevent injury if subject to excessive force.

SUMMARY

The present invention provides a brace having a liquid filled material that is transformed from a first soft state to a hardened second state upon application of a force exceeding a threshold force. The force can be internal or external.

In one aspect, the present invention provides an orthopedic brace for preventing injury to the wearer comprising a body having a series of liquid filled regions, the body having a first more flexible state wherein the liquid filled regions contain a liquid material and a second more rigid state wherein the liquid within the regions is hardened to a second harder state. The body is transformable from the first state to the second state upon receiving a force which exceeds a predetermined value.

The force can be an external force or an internal force applied to the body.

In one embodiment, the liquid filled regions are enclosed compartments arranged in a substantially vertical orientation. In another embodiment, the liquid filled elements are enclosed compartments arranged in a substantially horizontal orientation. In another embodiment, the liquid filled elements are compartments arranged in a substantially diagonal orientation.

In some embodiments, at least one sensor is positioned in or on the body to detect the force applied to the body. The sensor can measure the applied force and send a signal to activate the liquid if the force exceeds the predetermined value In some embodiments, the liquid is transformed to a more rigid state by a chemical reaction effected by mixing with a second liquid. In other embodiments, the liquid is transformed to a more rigid state by an isothermal process, i.e., effected by changing the temperature of the liquid.

In some embodiments, a second liquid is pumped into the liquid filled compartments to cause hardening of the liquid. In other embodiments, the second liquid is mixed with the liquid in the compartments by rupturing of a membrane containing the second liquid.

In accordance with another aspect, the present invention provides an orthopedic brace for preventing injury to a joint of a wearer, the brace comprising a body having a series of liquid filled regions positioned internal of an outer surface of the body. The body has a first more flexible state wherein the liquid filled regions contain a liquid material and a second more rigid state wherein the liquid within the regions undergoes a phase transformation to a solid state to transform the flexible brace to a rigid protective device to withstand further impact on the joint of a wearer of the brace. The body is transformable from the first state to the second state upon receiving a force which exceeds a preset value. At least one sensor is carried by the body for detecting and measuring at least one of an external or an internal force applied to the brace and determining if such force exceeds the preset value. The at least one sensor sends a first signal to effect transformation of the liquid to the solid state if the force exceeds the preset value and refrains from sending the first signal if the force does not exceed a preset value so that the liquid is maintained in its liquid state and the brace is not transformed to the more rigid state to maintain the mobility of the wearer.

In some embodiments, the at least one sensor comprises a plurality of sensors carried by the body and spaced apart to detect impact to various regions of the body. In some embodiments, the phase change is an isothermal process; in other embodiments, the phase change is caused by a chemical reaction. In some embodiments, the chemical reaction is effected by mixing of a second liquid within the liquid filled regions.

In accordance with another aspect of the present invention, a method for protecting a joint of the wearer from an excessive force applied to the joint is provided, the method comprising:

providing a brace having a liquid filled section;
measuring an external or an internal force applied to the brace;

comparing the applied external or internal force to a predetermined value; and transforming the liquid filled section to a solid filled section to rigidify the brace if the measured applied force exceeds the predetermined value.

In some embodiments, the liquid filled section includes a plurality of compartments containing the liquid therein. In some embodiments, the brace includes a sensor, and the sensor measures the applied external or internal force. In some embodiments, the sensor sends a signal to an activator if the applied force exceeds a predetermined value.

BRIEF DESCRIPTION OF THE DRAWINGS

Preferred embodiment(s) of the present disclosure are described herein with reference to the drawings wherein:

FIG. 1A is a side perspective view of a knee brace of a first embodiment of the present invention, shown in a flexible state and with the liquid columns (compartments) positioned in a substantially vertical orientation;

FIG. 1B is a side perspective view similar to FIG. 1A showing the knee brace in the hardened state;

FIG. 1C is a cross-sectional view taken along line 1C-1C of FIG. 1A;

FIGS. 5A and 5B show respectively a rotation force and a direct force applied to the knee causing the brace to transform to a hardened state, and further showing the sensors in phantom lines which are omitted from FIGS. 1-4B for clarity;

FIG. 6 is a side perspective view of an alternate embodiment of the knee brace of the present invention;

FIG. 7 is a side perspective view of another alternate embodiment of the knee brace of the present invention;

DETAILED DESCRIPTION OF PREFERRED EMBODIMENTS

Figure 2:
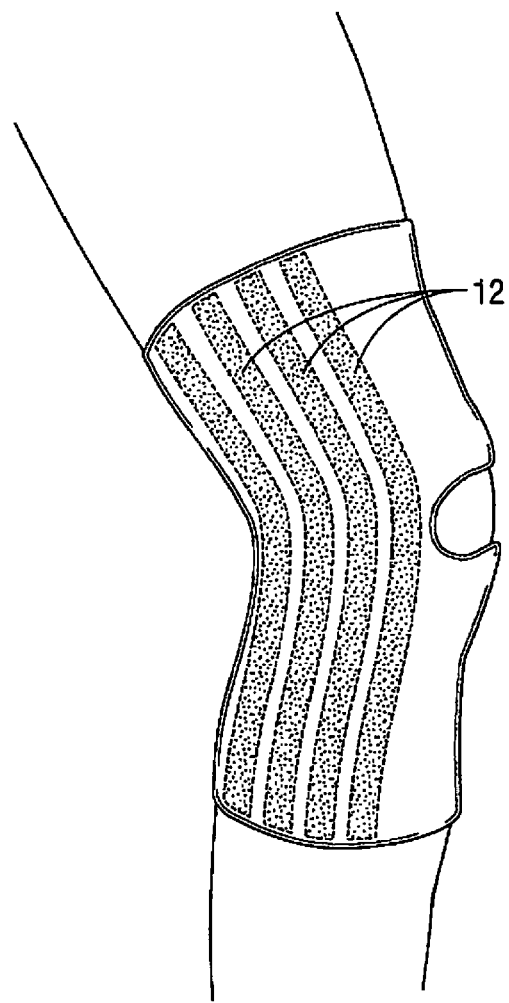
FIG. 2 is a side perspective view of the knee brace of FIG. 1A shown positioned on a person's knee.

Referring now in detail to the drawings where like reference numerals identify similar or like components throughout the several views, several different embodiments of the orthopedic braces of the present invention are described herein.

The braces of the present invention are designed to be placed over the joint, e.g., ankle or knee, in a flexible state, and maintained in such state. The brace remains in the flexible state until it receives a sufficient impact, at which point it transforms to a more rigid state to protect the joint. This is achieved by a transformation of the liquid within the brace to a solid state. Various ways to cause the phase change from liquid to solid are disclosed herein by way of example, although other ways to achieve such phase transformation can be utilized. The braces include liquid contained in columns or compartments which provide flexibility to the brace so as not to inhibit the wearer's mobility. When the brace is transformed to the hardened state, the columns form a rigid structure which thereby protects the joint. Thus, automatically, the brace is transformed from a flexible brace in which the wearer's motion and mobility are not affected so the wearer can participate uninhibited/unrestrained in activities, including athletic activities, to a rigid state which effectively "locks" the brace and limits movement/motion, thus protecting the joint. As can be appreciated, the present invention therefore provides a protective rigid brace on an automatic as needed basis.

Note that where there are multiple identical components in the particular Figure, e.g., sensors, compartments, only a few are labeled for clarity.

Turning now to a first embodiment of the knee brace of the present invention, and with reference to FIGS. 1A-2, the knee brace is designated generally by reference numeral 10 and includes a plurality of columns or compartments 12 embedded in the wall of the brace 10 between an outer wall 14 and an inner wall 16. Contained within the columns 12 is a liquid 18. The liquid is preferably a liquid metal. One type of metal that can be utilized is gallium which undergoes a phase transformation in response to temperature change. Other metals are also contemplated. Alternatively, the liquid can be a polymer or plastic which undergoes a phase transformation upon temperature change, provided the hardened state of such material is sufficient to protect the knee. As an alternative to temperature change to effect transformation from a liquid to a solid, chemical reactions are also contemplated such as by impact or as a result of the mixing of two liquids. These are discussed in more detail below. In the liquid state, the brace 10 remains flexible so as to not adversely affect mobility of the wearer.

Figure 3A:
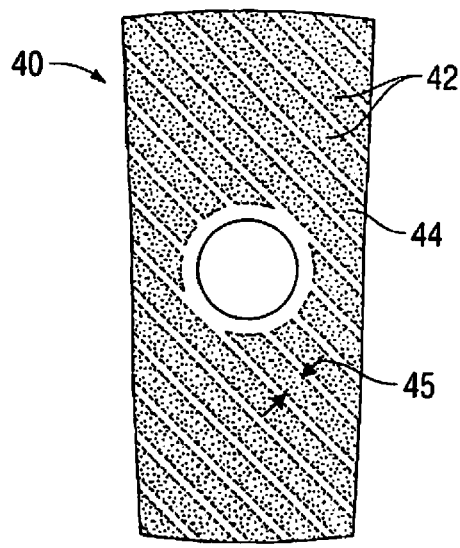
FIG. 3A is a front view of an alternate embodiment of the knee brace of the present invention having the liquid columns positioned in a substantially diagonal orientation, and shown in the flexible state.
Figure 3B:
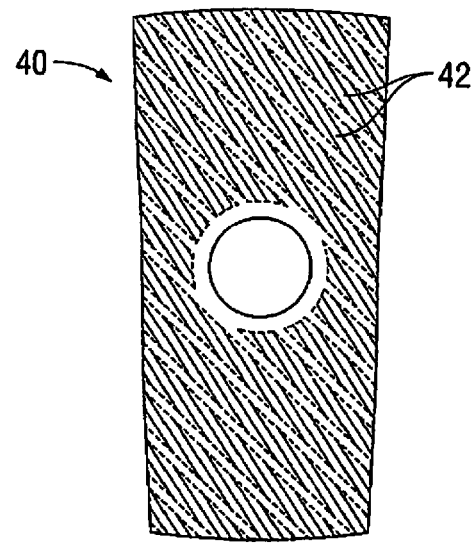
FIG. 3B is a front view similar to FIG. 3A showing the knee brace in the hardened state.
Figure 4A:
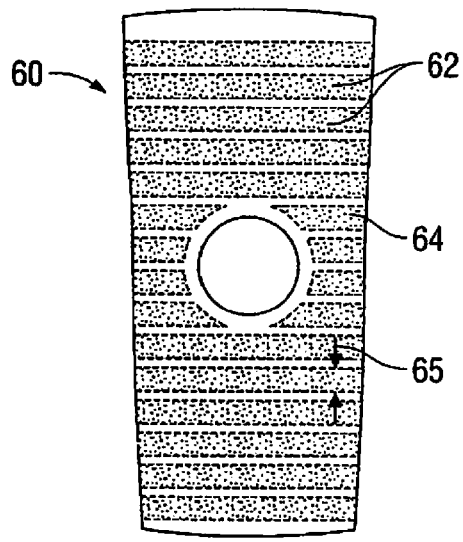
FIG. 4A is a front view of another alternate embodiment of the knee brace of the present invention having the liquid columns positioned in a substantially horizontal orientation, and shown in the flexible state.
Figure 4B:
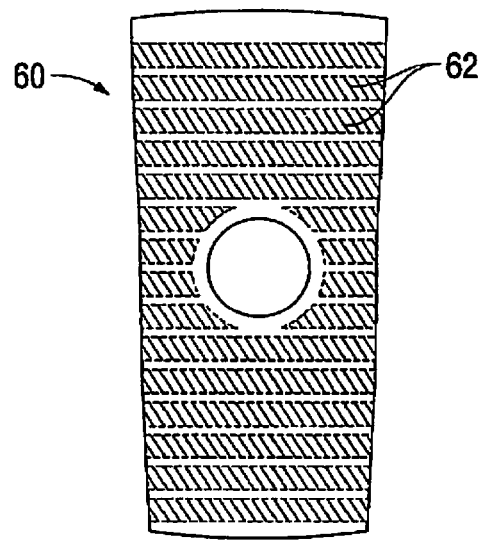
FIG. 4B is a front view similar to FIG. 4A showing the knee brace in the hardened state.
Figure 8:
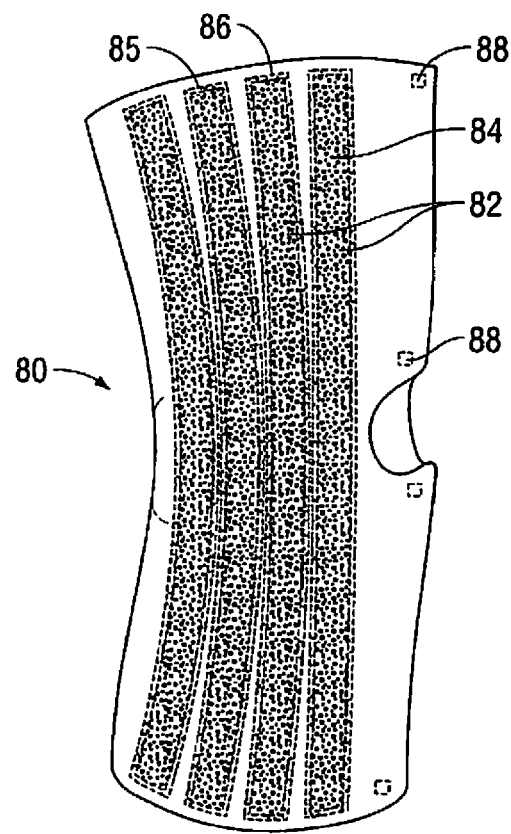
FIG. 8 is a side perspective view of another alternate embodiment of the knee brace of the present invention.
Figure 9A:
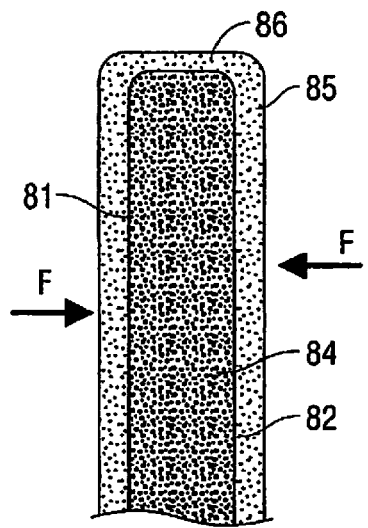
FIG. 9A is a close up view of a portion of the one of the compartments of the brace of FIG. 8 showing a force applied to the brace.
Figure 9B:
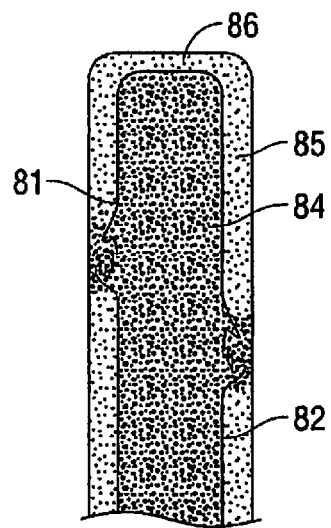
FIG. 9B is a view similar to FIG. 9A showing rupturing of the internal wall to cause mixing of a second material with the fluid in the compartment.
Figure 9C:
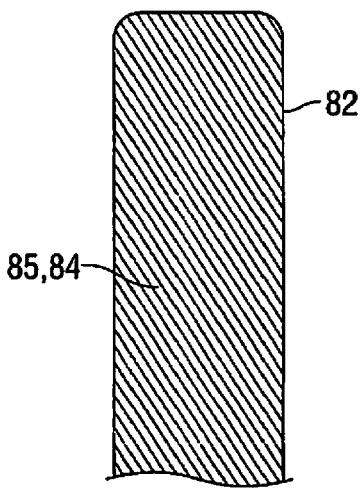
FIG. 9C is a view similar to FIG. 9A showing the fluid transformed to a hardened state within the compartment.

The columns 12 are shown extending substantially vertically, preferably extending the entire length, or substantially the entire length of the brace 10. Alternatively, the columns can extend in other orientations such as in a substantially diagonal orientation as in brace 40 of FIGS. 3A-3B or in a substantially horizontal orientation as in brace 60 of FIGS. 4A-4B. FIG. 1A illustrates the columns 12 filled with liquid in a liquid state to maintain the flexibility of the brace 10, the columns sealed to keep the liquid within the individual compartments. Likewise, FIG. 3A illustrates the sealed columns 42 filled with liquid 44 in a liquid state to maintain the flexibility of the brace 40 and FIG. 4A illustrates the sealed columns 62 filled with liquid 64 in a liquid state to maintain the flexibility of the brace 60. As shown, preferably the columns extend along or across the entire region of the brace so that the entire knee and adjacent regions are protected. However, it is also contemplated that the columns can extend less than the entire length or provided only in certain regions of the brace so that only select regions of the brace are solidified. Additionally, the columns 12, 42, and 62 are shown having a width 15, 45, and 65, respectively. However, it is also contemplated that the columns can have a shorter width, thereby enabling more columns to be provided, or have a wider width, providing fewer columns. Further, the columns need not be of uniform width, but can have varying width. Such varying width can provide regions of differing hardness to accommodate various regions of the knee, if desired.

FIGS. 5A and 5B illustrate the type of impact that can cause the hardening of the liquid within the compartments. In FIG. 5A a rotational force of sufficient magnitude will trigger a response for solidifying the liquid within the columns 12 (or columns 42 and 62). This rotation can be caused by an external impact or by internal impact on the brace such as by rotation or twisting of the wearer's knee. In FIG. 5B a direct impact, e.g., an external impact, of sufficient force will trigger hardening of the liquid within the columns 12 (or columns 42 and 62).

Figure 14:
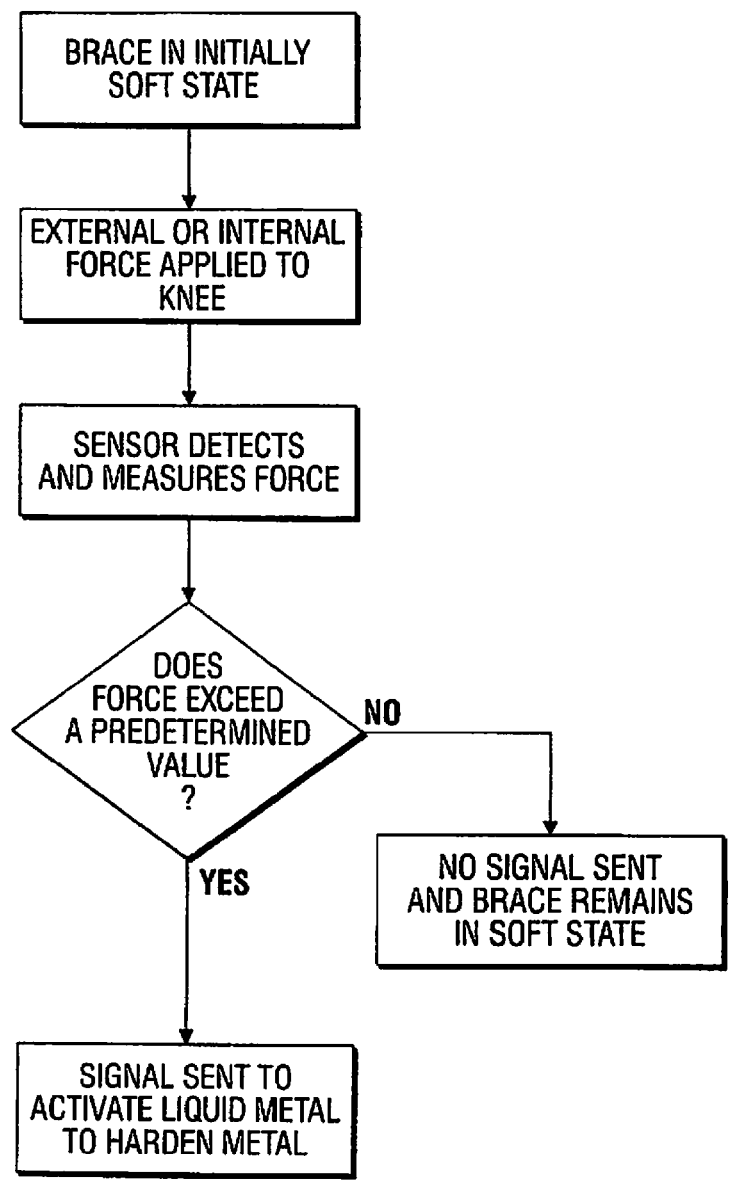
FIG. 14 is a flow chart illustrating the use of the knee brace of the present invention.

FIG. 14 provides a flow chart to explain generally the function and use of the brace 10. Note the flow chart explains the use of the brace with liquid metal, it being understood as noted above, that other hardenable non-metal materials can be utilized. With reference to FIG. 14, brace 10 is initially in a soft state. If an external or internal force if applied, a sensor within the brace 10, e.g., sensors 18 of FIGS. 5A and 5B, detects such force and measures the force. If the force does not exceed a preset threshold or predetermined value (magnitude), then the brace remains in its softer more flexible state and no signal is sent by the sensor to activate the metal. However, if the measured force exceeds a preset threshold/predetermined value, a signal is sent to a controller (not shown) position in or on the brace, to activate the liquid to transform it to a hardened state. Activation of the liquid to transform it to a hardened state can occur in a variety of different ways as described herein.

As shown in FIG. 6, one way to harden the liquid is to provide a cooling mechanism to cool the liquid. In this embodiment, sensors 38, like sensors 18 of FIG. 1, are positioned internally of brace 30, and located at various dispersed regions within the brace 30 to sense impact at the various regions. After detecting and measuring the force and determining it exceeds a predetermined or preset value, sensor 38 will send a signal to a controller (not shown). The controller in turn will send a signal to activate the cooling chambers 35 which surround each of the compartments 32. Such cooling of chambers 35 causes cooling of the liquid 34 in the liquid compartments 32. Upon cooling, the liquid 34 hardens, thereby forming rigid compartments and forming a protective somewhat cage-like structure. In the alternate embodiment of FIG. 7, brace 50 has a single cooling chamber 53 within the brace 50. This single cooling chamber 53 functions to cool the liquid within the compartments 52 when activated in response to the force detection by the sensors 58. The cooling chamber 53 can be provided within the wall of the brace 50 or alternatively formed internal of the internal wall of the brace 50. Alternatively, more than one cooling chamber can be provided to cool the brace 50. Brace 50 therefore differs from brace 30 in that in brace 30, each liquid filled compartment 32 is partially or fully surrounded by a cooling chamber while in brace 50, cooling of the chamber positioned within the brace 50 cools the entire brace which in turn cools the liquid within the compartments.

Figure 10:
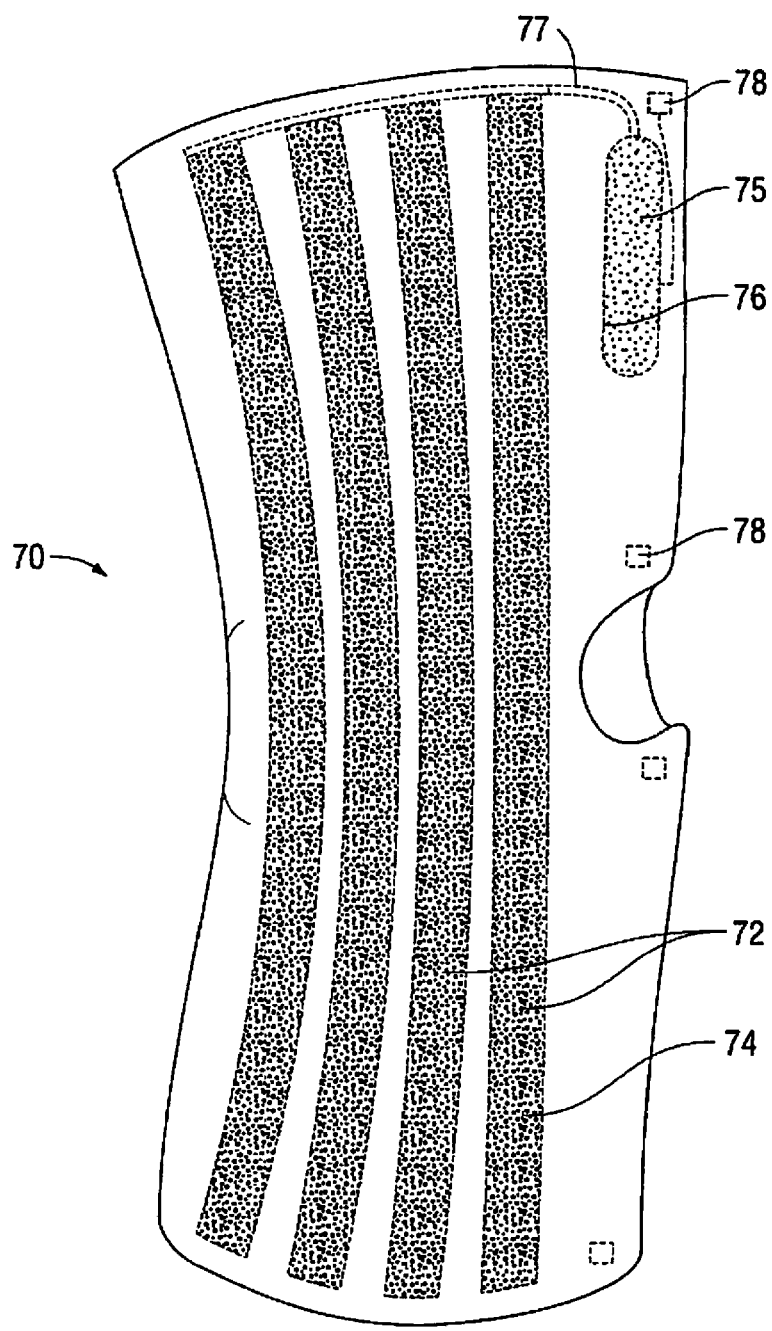
FIG. 10 is a perspective view of another alternate embodiment of the knee brace of the present invention.
Figure 11A:
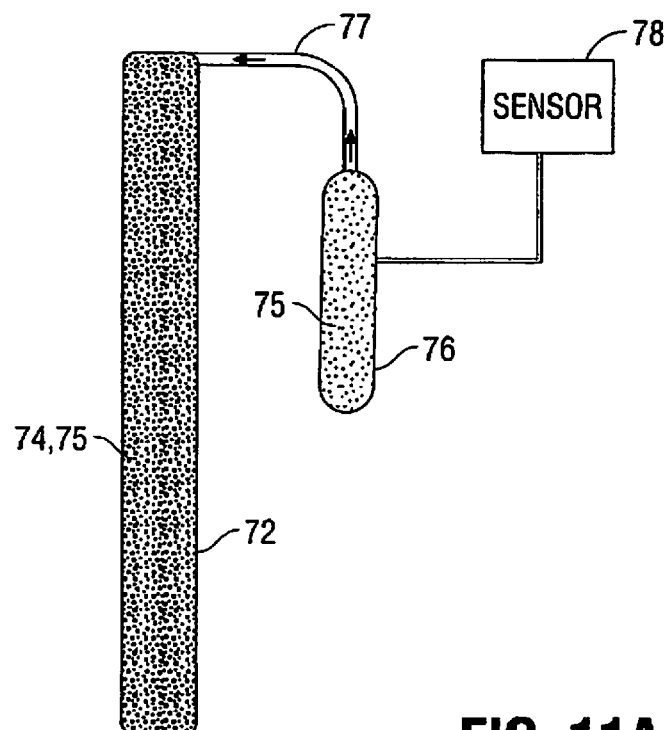
FIG. 11A is a close up view of the one of the compartments of FIG. 10, and showing schematically the sensor and the container for storing a second material.
Figure 11B:
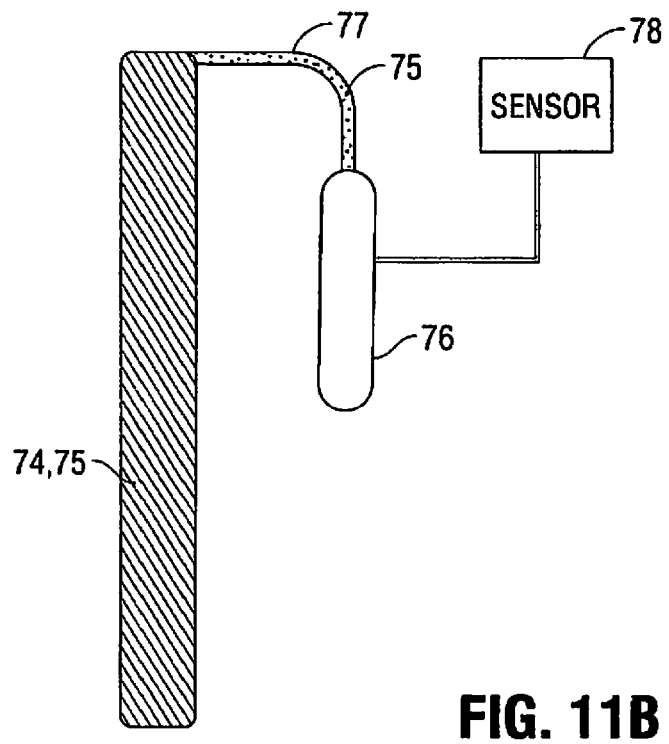
FIG. 11B is a view similar to FIG. 11A showing the liquid in the compartment transformed to a harder material as a result of mixing with the second material.

FIG. 10-11B illustrates another alternate way of transforming the liquid within the compartments of the brace. In this embodiment, sensors 78, positioned within brace 70, detect and measure the force of impact, or rotational force, and compare it to a predetermined or preset value. If it exceeds such value, a signal is sent to the pump within chamber 76 to actuate the pump for pumping liquid 75 from chamber 76 through tubing 77 into the liquid filled compartment 72. A valve can be provided to seal the compartments 72 until liquid 75 is pumped therein. Once the pumped liquid 77 mixes with the liquid 74 in the compartments 72, a chemical reaction causes a hardening of the material within the compartments 72 and thus transforms the flexible brace 70 into a hardened cage-like structure. Such activation of the liquid 74 within the compartments 72 is shown schematically in FIGS. 11A and 11B, which illustrate one of the plurality of compartments 12. If a sufficient force is detected by sensor 78, a signal is sent to activate a pump (not shown) within the chamber 76 to pump liquid 75 from chamber 76, through tubing 77, and into the chamber 72 containing liquid 74 to thereby mix liquid 75 with liquid 74. A single or multiple pumps and chambers can be provided.

As an alternate to a pump to mix a second liquid with the liquid in the compartments, a rupturable wall or membrane could be provided. The brace in this embodiment would avoid the need for sensors and a controller. In this embodiment, brace 80 has a series of inner compartments 82, each surrounded by an outer compartment 86, and sharing a common wall. That is, the external wall 81 of the inner compartment 82 forms the internal wall of outer compartment 86. Wall 81 is made of a material which ruptures when a sufficient force is applied. In this manner, upon application of a sufficient force, the wall (membrane) 81 would break, enabling the liquid 84 of compartment 82 to mix with the liquid 85 contained in the outer compartment 86. Such mixing of the liquids causes a chemical reaction which results in a phase transformation to harden the liquid.

In another embodiment, the liquid filled compartments are activated by an excessive bending or movement of the compartments which causes a chemical reaction as the movement (energy) provides a trigger for spontaneous transformation to a solid state. The liquid ferrous material in the compartments can also be activated for transformation into a solid state by electric charge, polarization or other inducement methods.

The braces disclosed herein in some embodiments can be manually returned to the relaxed liquid state, i.e., manually overriding the transformed solid state.

Note the control unit communicating with the sensors for controlling operation, i.e., controlling activation of the liquid through polarization, electric charge, pumping fluid, etc., can be software based and programmed to activate the liquid automatically in an as needed basis in response to signals received from the force detecting/measuring sensors.

Figure 12:
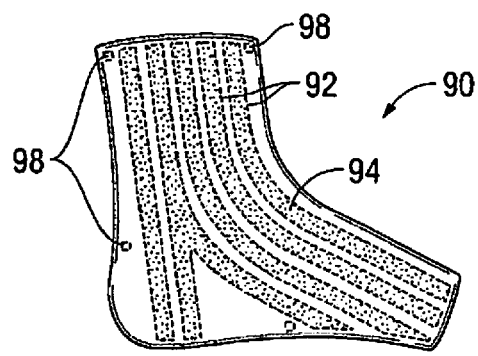
FIG. 12 is a perspective view of an ankle brace of the present invention, shown in a flexible state and with the liquid columns (compartments) positioned in a substantially vertical orientation.
Figure 13A:
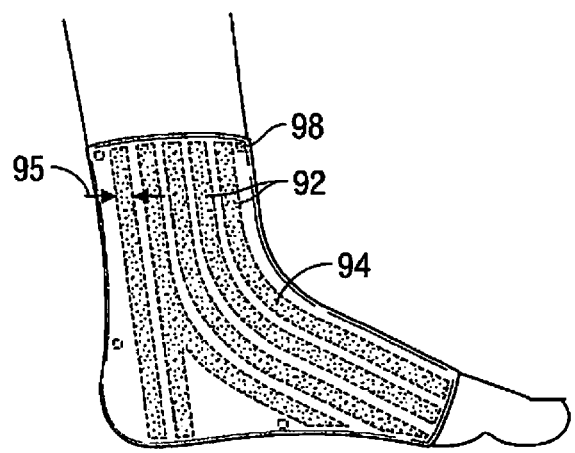
FIG. 13A is a perspective view of the ankle brace of FIG. 12 shown on a person's ankle in a flexible state.
Figure 13B:
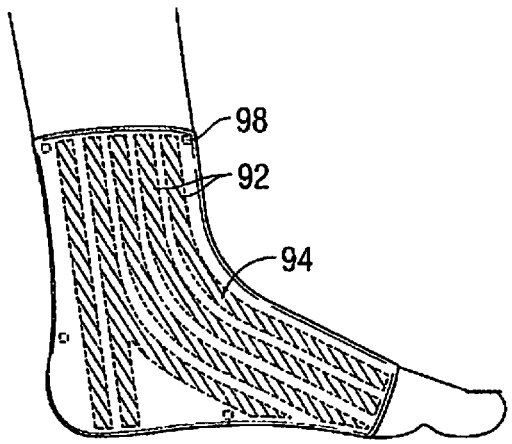
FIG. 13B is a perspective view similar to FIG. 12 showing the ankle brace in the hardened state.

FIGS. 12-13B illustrate an alternate embodiment of the brace for use in supporting a person's ankle. In this embodiment, ankle brace 90 is similar to the brace 10 of FIG. 1, except it is shaped to be fitted on a user's ankle. That is, brace 90 has a plurality of liquid filled compartments 92. The liquid 94 can be a metal or non-metal as described above with respect to the knee braces. The liquid can be transformed to a harder state in any of the ways described above and thus the brace 80 can include sensors 98, similar to the sensors 18 of FIG. 5A (or similar to sensors 38 or 88), which are spaced apart internally within the brace 90. Cooling, fluid mixing, or other methods to harden the liquid can be utilized in the ankle brace in the same way as in the knee brace to transform the ankle brace from the softer more flexible state of FIG. 13A to the harder more rigid state of FIG. 13B. The flow chart of FIG. 14 is likewise applicable to the ankle brace 90 of FIG. 12.

The compartments 92 of brace 90 are shown extending vertically in the ankle region, but alternatively can extend diagonally, horizontally, or in other directions as in the knee brace described above. As shown, preferably the columns extend along or across the entire region of the brace so that the entire ankle and adjacent regions are protected. However, it is also contemplated that the columns can extend less than the entire length or provided only in certain regions of the brace so that only select regions of the brace are solidified. Additionally, the columns 92 are shown having a width 95. However, it is also contemplated that the columns can have a shorter width, thereby enabling more columns to be provided, or have thicker width, providing fewer columns. Further, the columns need not be of uniform width, but can have varying width. Such varying width can provide regions of differing hardness to accommodate various regions of the ankle and adjacent regions, if desired.

Note for simplicity the sensors are not shown on all the Figures, it being understood that Figures illustrating views of the same embodiment would have the sensors. Also, the sensors illustrated are just one example of how the sensors are positioned, it being understood that a different number of sensors and different locations are also contemplated.

While the above description contains many specifics, those specifics should not be construed as limitations on the scope of the disclosure, but merely as exemplifications of preferred embodiments thereof. For example, those skilled in the art will envision many other possible variations that are within the scope and spirit of the disclosure as defined by the claims appended hereto.

What is claimed is:

1. A method of protecting a joint of a wearer from an excessive force applied to the joint during an athletic activity to prevent injury, the method comprising:
    placing over the joint of the wearer a protective brace having a liquid filled section, the protective brace having a first state in which the wearer's motion and mobility are not affected so the wearer can participate in unrestrained activities;
    measuring an external impact force applied to the brace during the athletic activity by a sensor on the protective brace; and
    comparing the measured impact force to a predetermined value to determine if excess impact force has been applied, and a) if the measured impact force does not exceed the predetermined value, the protective brace remains in the first state to retain the mobility of the wearer and the wearer can participate uninhibited and unrestrained in activities; b) if the measured impact force exceeds the predetermined value, the protective brace transforms to a second solid state wherein the liquid filled section is transformed to a solid section to rigidify and lock the brace to protect the wearer during the athletic activity and limit movement and motion of the wearer to protect the joint of the wearer.

2. The method of claim 1, wherein the protective brace is placed over a knee of the wearer.

3. The method of claim 1, wherein the protective brace is placed over an ankle of the wearer.

4. The method of claim 1, further comprising the step of returning the protective brace to the first state after transforming to the second state.

5. The method of claim 1, wherein the liquid filled section includes a plurality of compartments containing the liquid therein and the liquid within the compartments is transformed to solid.

6. The method of claim 5, wherein the compartments are enclosed and arranged in a substantially vertical orientation.

7. The method of claim 5, wherein the compartments are enclosed and arranged in a substantially horizontal orientation.

8. The method of claim 5, wherein the compartments are enclosed and arranged in a substantially diagonal orientation.

9. The method of claim 5, wherein a second liquid is pumped into the compartments to transform the protective brace to the second solid state, the pump activated by a signal from the sensor.

10. The method of claim 5, wherein a second liquid is mixed with the liquid in the compartments by rupturing of a membrane containing the second liquid.

11. The method of claim 5, wherein the compartments are arranged in columns having varying width to provide regions of varying hardness.

12. The method of claim 5, further comprising cooling chambers around the compartments to cool the liquid in the compartments if the measured impact force exceeds the predetermined value.

13. The method of claim 1, further comprising a tubing in fluid communication with the liquid, wherein the liquid is transformed to the second solid state by a chemical reaction effected by mixing with a second liquid infused through the tubing.

14. The method of claim 1, wherein the liquid is transformed to the solid state by a change in temperature of the liquid.

15. The method of claim 1, wherein the step of measuring the external impact force is performed by a plurality of sensors carried by the protective brace and spaced apart to detect impact to various regions.

16. The method of claim 1, wherein the liquid is contained in columns and its transforming to the second solid state is an isothermal process.

17. The method of claim 1, wherein transformation to the second solid state is caused by a chemical reaction.

18. The method of claim 17, wherein the chemical reaction is effected by mixing of a second liquid with the liquid filled section.

* * * * *